United States Patent
Job

(10) Patent No.: US 7,154,003 B2
(45) Date of Patent: Dec. 26, 2006

(54) PROCESS FOR PREPARING PHTHALOYL CHLORIDE

(75) Inventor: Andreas Job, Köln (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 11/128,630

(22) Filed: May 13, 2005

(65) Prior Publication Data

US 2005/0277788 A1    Dec. 15, 2005

(30) Foreign Application Priority Data

May 17, 2004    (DE)    ........................ 10 2004 024 807

(51) Int. Cl.
*C07C 51/58*    (2006.01)

(52) U.S. Cl. .................................................... 562/854

(58) Field of Classification Search ..................... None
See application file for complete search history.

(56) References Cited

U.S. PATENT DOCUMENTS

| | | | |
|---|---|---|---|
| 2,051,096 A | 8/1936 | Mares | 260/123 |
| 3,318,950 A | 5/1967 | Christoph et al. | 260/544 |
| 3,758,570 A | 9/1973 | Findelsen et al. | 260/544 C |
| 3,810,940 A | 5/1974 | Hauser | 260/544 |
| 4,880,576 A | 11/1989 | Blank et al. | 562/828 |
| 5,623,082 A | 4/1997 | Decker et al. | 554/231 |
| 6,206,819 B1 | 3/2001 | Graves et al. | 582/855 |

FOREIGN PATENT DOCUMENTS

WO    2004/022520    3/2004

OTHER PUBLICATIONS

J. Am. Chem. Soc. 1937, vol. 59, pp. 206-208; "Phthalyl Chloride" L.P. Kyrides.
Can. J. Chem. 1970, 48, pp. 3566-3571; "Structure of a diazecine derivative from the condensation of phthaloyl chloride with enthylenediamine" S. Wolfe and S. Hasan Database CA 'Online! Chemical Abstracts Service, Columbus, Ohio, US.
"Carboxylic acid chlorides" XP002341528 gefunden im STN; Database accession No. 1982: 19845 *Zusammenfassung * & JP 56 103131 A2 (Mitsui Toatsu Chemicals, Inc., Japan) Aug. 18, 1981.

*Primary Examiner*—Paul A. Zucker
(74) *Attorney, Agent, or Firm*—Jennifer R. Sang

(57) ABSTRACT

The invention relates to a novel process for preparing phthaloyl chloride (benzene-1,2-dicarbonyl chloride) by reacting phthalic anhydride with phosgene in the presence of a specific N,N-disubstituted formamide as a catalyst.

18 Claims, No Drawings

PROCESS FOR PREPARING PHTHALOYL CHLORIDE

The invention relates to a novel process for preparing phthaloyl chloride (benzene-1,2-dicarbonyl chloride) from phthalic anhydrid Typically, phthaloyl chloride is prepared from phthalic anhydride by reacting with various agents for the introduction of chlorine ("chlorinating agents").

According to U.S. Pat. No. 2,051,096, phthaloyl chloride is obtained by reacting phthalic anhydride with a substance which bears at least two chlorine atoms on a carbon atom in the presence of a catalyst such as zinc chloride, aluminium chloride or iron chloride. Preference is given to working with use of trichloromethane or tetrachloromethane. However, this reaction entails very high temperatures in the range of 250 to 300° C. In addition, trichloromethane and tetrachloromethane are nowadays very problematic reaction components for industrial purposes.

J. Am. Chem. Soc. 1937, 59, 206–208 describes the preparation of phthaloyl chloride by reacting phthalic anhydride with thionyl chloride or benzotrichloride in the presence of anhydrous zinc chloride. However, this reaction also entails high temperatures. In addition, yield and quality of the product in this method are not entirely satisfactory. In particular, the desired phthaloyl chloride product still contains certain amounts of dissolved phthalic anhydride.

According to Can. J. Chem. 1970, 48, 3566–3571, phthaloyl chloride can also be obtained by reacting phthalic anhydride with phosphorous(V) chloride (phosphorous pentachloride), but likewise with an only unsatisfactory yield of 54% of the desired product.

According to DE-A 20 36 171, phthaloyl chloride can be obtained by reacting phthalic anhydride with trichloromethyl isocyanide dichloride in the presence of iron(III) chloride. However, chlorocarbonyl isocyanide dichloride is formed in this reaction as a coproduct.

EP-A-0 050 779 describes the use of N,N-dialkylated formamides as accelerants in the exchange of hydroxyl groups in organic compounds for chlorine or bromine and as a catalyst for the reaction of phenolic compounds with phosgene to give arylchloroformic esters.

Moreover, U.S. Pat. No. 3,810,940 describes the reaction of intramolecular anhydrides with phosgene in an inert aromatic solvent, for which the catalyst used is a carboxamide of the formula RCONR'$_2$ in which R is hydrogen or a lower alkyl group having preferably 1–4 carbon atoms and R' is likewise a lower alkyl group having preferably 1–4 carbon atoms. Especially in the case of the preparation of unsubstituted cyclic aromatic diacid chlorides from the corresponding intramolecular anhydrides, only an incomplete conversion is achieved here. Explicitly described is the reaction of phthalic anhydride with phosgene in chlorobenzene in the presence of N,N-dimethylformamide as a catalyst. However, the resulting conversion is not satisfactory. Since it is not possible, owing to the boiling point differential between the desired phthaloyl chloride product and the phthalic anhydride starting material being too low, to remove the starting material distillatively from the product, a very high conversion is essential for a good product quality.

WO-A-04/022520 discloses a further process for preparing phthaloyl chloride by reacting phthalic anhydride with phosgene in an inert solvent in the presence of an N,N-dialkylformamide. A characteristic of this process is that the formamide and/or phosgene is metered in continuously or semicontinuously. Substituents of the formamides which are specified are quite generally straight-chain or branched alkyl radicals. Preferred radicals which are specified are straight-chain or branched $C_1$–$C_{10}$-alkyl, in particular $C_1$–$C_6$-alkyl. However, explicit mention is made exclusively of N,N-dialkylformamides having in each case two identical $C_1$–$C_4$-alkyl substituents on the nitrogen. The N,N-dimethylformamide (DMF) and N,N-dibutylformamide (DBF) catalysts used exclusively in the examples lead in the process described to undesired secondary components, the carbamoyl chlorides. The dimethylcarbamoyl chloride formed when DMF is used is known to be a carcinogenic substance and is therefore highly undesired in industrial plants and chemical formulations. The dibutylcarbamoyl chloride which is formed when DBF is used and is less toxic has a similar boiling point to the phthaloyl chloride product to be prepared and can thus only be separated from it by distillation with considerable difficulty. In addition, the products prepared by this route exhibit an undesired dark violet colour.

It is thus an object of the invention to provide an improved process by which phthaloyl chloride can be obtained in very good yields from a readily available starting material such as phthalic anhydride using readily available assistants, with acceptable energy intensity and in particular with avoidance of the occurrence of relatively large amounts of undesired by-products.

It has been found that, surprisingly, starting from phthalic anhydride with use of phosgene as an agent for the introduction of chlorine in the presence of specific types of N,N-disubstituted formamides, the desired phthaloyl chloride product can be obtained in high yields and in very good purity, and carcinogenic by-products in particular can be avoided.

The present invention thus provides a process for preparing phthaloyl chloride of the formula (I)

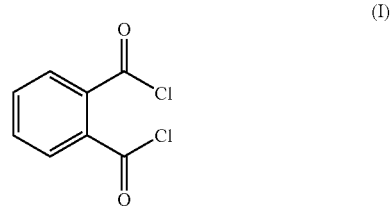

in which phthalic anhydride of the formula (II)

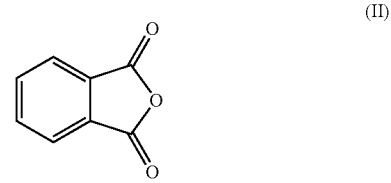

is reacted with phosgene in the presence of a catalyst, this process being characterized in that the catalyst used is an N,N-disubstituted formamide of the general formula (III)

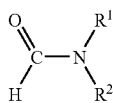

(III)

in which
R¹ and R² are each independently
straight-chain or branched $C_1$–$C_{22}$-alkyl or straight-chain or branched $C_2$–$C_{22}$-alkenyl,
$C_3$–$C_8$-cycloalkyl,
$C_6$–$C_{10}$-aryl or
$C_7$–$C_{12}$-arylalkyl where, in the case that each R¹ and R² radical is independently straight-chain or branched $C_1$–$C_{22}$-alkyl or straight-chain or branched $C_2$–$C_{22}$-alkenyl, the total molecular weight of the N,N-disubstituted formamide has to be at least 269 g/mol.

The phthalic anhydride of the formula (II) to be used as a starting material in the process according to the invention is a known commercial synthetic chemical.

The phosgene used as an agent for the introduction of chlorine is likewise known and can be used in commercial qualities.

In the N,N-disubstituted formamides of the general formula (III) used in the process according to the invention, the substituents listed are defined as follows:

Straight-chain or branched $C_1$–$C_{22}$ is a straight-chain or branched alkyl radical having from 1 to 22 carbon atoms such as methyl, ethyl, and straight-chain or branched propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl or docosyl radicals.

Straight-chain or branched $C_2$–$C_2$-alkenyl is a straight-chain or branched alkenyl radical having from 2 to 22 carbon atoms, for example vinyl (—CH=CH₂), n-prop-1-en-1-yl (—CH=CH—CH₃), allyl (—CH₂—CH=CH₂), n-but-1-en-1-yl (—CH=CH—CH₂—CH₃), n-but-2-en-1-yl (—CH₂—CH=CH—CH₃), oleyl (—(CH₂)₈—CH=CH—(CH₂)₇—CH₃) or linoleyl (—(CH₂)₈—CH=CH—CH₂—CH=CH—(CH₂)₄—CH₃)

When R¹ and R² are each straight-chain or branched $C_1$–$C_{22}$-alkyl or straight-chain or branched $C_2$–$C_{22}$-alkenyl, the total molecular weight of the resulting N,N-disubstituted formamide of the formula (III) has to be at least 269 g/mol.

While complying with the aforementioned proviso of a total molecular weight of at least 269 g/mol, R¹ and R² in a preferred combination are each independently a straight-chain or branched $C_8$–$C_{22}$-alkyl or -alkenyl radical, more preferably a straight-chain or branched $C_8$–$C_{20}$-alkyl or -alkenyl radical, and both R¹ and R² radicals are especially preferably each the same straight-chain or branched $C_8$–$C_{18}$-alkyl- or -alkenyl radical.

While complying with the aforementioned proviso of a total molecular weight of at least 269 g/mol, in a further preferred combination, R₁ is a straight-chain or branched $C_1$–$C_4$-alkyl radical such as methyl, ethyl, n-propyl, isopropyl, n-butyl, isobutyl or tert-butyl, and R² is a straight-chain or branched $C_8$–$C_{22}$-alkyl or -alkenyl radical, in particular a straight-chain or branched $C_{11}$–$C_{20}$-alkyl or -alkenyl radical.

In the general formula (III), $C_3$–$C_8$-cycloalkyl is cyclopropyl, cyclobutyl, cyclopentyl, cyclohexyl, cycloheptyl or cyclooctyl. Preference is given to: cyclopropyl, cyclopentyl and cyclohexyl.

In a preferred combination, R¹ and R² are each independently a $C_3$–$C_8$-cycloalkyl radical, both R¹ and R² radicals are preferably each the same $C_3$–$C_8$-cycloalkyl radical and both R¹ and R² radicals are in particular each a cyclopentyl or a cyclohexyl radical.

In the general formula (III), $C_6$–$C_{10}$-aryl is an aromatic radical having from 6 to 10 carbon atoms. Preferred aryl radicals are phenyl and naphthyl.

In the general formula (III), $C_7$–$C_{12}$-arylalkyl is a benzyl, phenylethyl, phenylpropyl, naphthylmethyl or a naphthylethyl radical.

Examples of N,N-disubstituted formamides of the general formula (III) include:
N,N-dioctylformamide,
N,N-dinonylformamide,
N,N-didecylformamide,
N,N-diundecylformamide,
N,N-didodecylformamide,
N,N-ditridecylformamide,
N,N-ditetradecylform amide,
N,N-dipentadecylformamide,
N,N-dihexadecylformamide,
N,N-dioctadecylformamide (=N,N-distearylamide)
N-methyl-N-stearylformamide,
N-ethyl-N-stearylformamide,
N,N-dicyclopentylformamide,
N,N-dicyclohexylformamide,
N,N-dibenzylformamide,
N-methyl-N-benzylformamide,
N-methyl-N-naphthylmethylformamide.

The N,N-disubstituted formamides are known organic synthetic chemicals or reagents which are commercially available. Employing the principle of the process described in EP-A-0 050 779, it is also possible to prepare them by reacting the corresponding amine of the formula HNR¹R² with formic acid at elevated temperature. This reaction can be carried out without, but also with, inert solvent. Useful inert solvents are the same solvents which are mentioned below for the inventive reaction. The reaction mixture obtained in the reaction of amine of the formula HNR¹R² and formic acid may be used directly for the inventive reaction without the N,N-disubstituted formamide having to be isolated beforehand.

The process according to the invention is typically carried out within a temperature range of 20 to 150° C., preferably of 40 to 120° C. and in particular of 55 to 100° C.

The process according to the invention is generally carried out under standard pressure. However, it is also possible to carry out the process according to the invention under elevated or reduced pressure, generally in a range of from 0.1 to 50 bar, preferably in a range of from 1 to 10 bar.

To carry out the process according to the invention, generally 1.0 mol to 3.0 mol, preferably 1.4 mol to 2.2 mol, of phosgene are used for 1 mol of phthalic anhydride of the formula (II).

Moreover, based on 1 mol of phthalic anhydride of the formula (II), a total of 0.01 to 0.20 mol, preferably 0.02 to 0.10 mol, of N,N-disubstituted formamide of the formula (III) is used.

The process according to the invention can be performed practically in various ways.

Thus, there are several variants for the metered addition of the phosgene and of the catalyst: in one variant, the phthalic anhydride is initially charged in the reaction vessel and the phosgene and the catalyst are each independently metered in continuously or "semi-continuously".

In the context of the present invention, continuously means that the particular reaction component (phosgene and/or the N,N-disubstituted formamide) is metered into the reaction mixture continually and uniformly over the entire reaction time.

In the context of the present invention, "semi-continuous" means that the particular reaction components (phosgene and/or the N,N-disubstituted formamide) is metered into the reaction mixture in portions, divided between defined time intervals. The individual portions are preferably of equal size and the individual time intervals preferably of equal length.

In one variant, both the phosgene and the N,N-disubstituted formamide of the formula (III) are metered in continuously.

In another variant, both the phosgene and the N,N-disubstituted formamide of the formula (III) are metered in "semi-continuously", divided between several portions.

In a further variant, the phosgene is metered in continuously, while the N,N-disubstituted formamide of the formula (III) is metered in "semi-continuously", divided between several portions.

In a further variant, the phosgene is metered in "semi-continuously", divided between several portions, while the N,N-disubstituted formamide of the formula (III) is metered in continuously.

Preference is given to initially charging the phthalic anhydride dissolved in an inert solvent.

Useful inert solvents are in particular: hydrocarbons such as pentane, hexane, heptane, octane, cyclohexane, methylcyclohexane, benzene, toluene, xylene, and halogenated hydrocarbons such as dichloromethane, trichloromethane, tetrachloromethane, chlorobenzene or dichlorobenzene. Toluene and chlorobenzene are particularly preferred as inert solvents. However, it is also possible to use the phthalic anhydride dissolved in pthaloyl chloride as a solvent.

Typically, the N,N-disubstituted formamide of the formula (III) is likewise metered in dissolved in an inert solvent, in which case useful solvents are those already mentioned and preference is given to selecting the same one as for the phthalic anhydride.

However, it is also possible to meter in the N,N-disubstituted formamide of the formula (III) without solvent. When it is a solid, it is preferably first melted and then metered in as a melt.

In a further embodiment of the process according to the invention, the phthalic anhydride is initially charged in an inert solvent together with the entire amount or a portion of the N,N-disubstituted formamide of the formula (III). Particularly for N,N-dicyclohexylformamide, it has been found to be useful to initially charge the entire amount together with the phthalic anhydride in the reaction vessel, then to heat this mixture to the reaction temperature and then to meter in the phosgene continuously or "semicontinuously". However, it has also been found to be useful to initially charge a portion of up to 2 mol % of the N,N-disubstituted formamide of the formula (III) together with the phthalic anhydride, then to heat the mixture to the reaction temperature and then to meter in the phosgene and the remaining amount of the N,N-disubstituted formamide of the formula (III), in each case either continuously, divided over the whole reaction time, or "semi-continuously".

In a further embodiment, it is possible to initially charge the phthalic anhydride in molten form without solvent and subsequently to continuously or semicontinuously meter in the phosgene and the N,N-disubstituted formamide of the formula (III), the latter likewise without solvent and in optionally molten form.

In each case, a particularly advantageous reaction time is of 5 to 15 hours which can be varied correspondingly depending on the batch size.

It is particularly advantageous to undertake metered addition of the N,N-disubstituted formamide of the formula (III) every 15 to 90 minutes and to meter in the phosgene continuously or "semi-continuously".

After the end of the addition of phosgene and N,N-disubstituted formamide of the formula (III), the reaction mixture is advantageously kept at the reaction temperature specified for another 1 to 3 hours and subsequently worked up by distillation under reduced pressure. After this distillation, the phthaloyl chloride is obtained in high yield and in very good quality. In particular, the product only has a small fraction of unconverted phthalic anhydride; this fraction is preferably less than 3% by weight. As a particular advantage over the prior art processes, it should also be emphasized that the N,N-disubstituted formamides used in accordance with the invention and the coproducts resulting therefrom, owing to the substantially higher boiling point, remain in the bottoms in the distillation. In addition, the resulting product is colourless in all cases, while only violet-coloured product which thus cannot be used without further complicated workup is obtained in the prior art processes, albeit at very good yields.

PREPARATION EXAMPLES

In all examples, phthalic anhydride having a content of at least 99% is used.

Example 1 (Inventive)

N-Methylstearylformamide as the Catalyst 523.7 g (3.5 mol) of phthalic anhydride and 5.5 g (0.02 mol) of N-methylstearylformamide as the catalyst are initially charged in 2203 ml of toluene and the mixture is heated to 75° C. At this temperature, 586.1 g (5.93 mol) of phosgene at an introduction rate of 97.7 g of phosgene per hour and simultaneously 59.97 g of N-methylstearylformamide dissolved in 92.1 ml of toluene are added continuously (i.e. 10 g of 100% N-methylstearylformamide per hour) over 6 hours. On completion of the metered addition of phosgene and catalyst, the mixture is stirred at 75° C. for another 1.5 hours.

To remove excess phosgene, 2150.7 g of distillate are removed at 55° C. and 60 mbar.

The crude product remains as a dark oil. It contains 86.6% by weight of phthaloyl chloride and 3.2% by weight of phthalic anhydride. This corresponds to a crude yield of 95% of theory.

After fine distillation 110 to 122° C. and 1.4 to 1.7 mbar, 659.9 g of colourless distillate having a product content of 97.4% by weight are obtained as the main fraction.

Example 2 (Comparative Example: N,N-Dibutylformamide as the Catalyst)

523.7 g (3.5 mol) of phthalic anhydride and 2.75 g (0.02 mol) of N,N-dibutylformamide as the catalyst are initially charged in 2203.4 ml of toluene, and the mixture is heated to 70° C. At this temperature, 586.1 g (5.93 mol) of phosgene at an introduction rate of 97.7 g of phosgene per hour and simultaneously 30.66 g of N,N-dibutylformamide dissolved in 218 ml of toluene are added continuously (5.1 g of N,N-dibutylformamide per hour) over 6 hours. On completion of the metered addition of phosgene and catalyst, the mixture is stirred at 70° C. for a further 1.5 hours.

To remove excess phosgene, 2103.0 g of distillate are removed at 55° C. and 60 mbar.

The crude product remains as a dark oil. According to HPLC analysis, it contains 83.8% by weight of phthaloyl chloride, 2.4% by weight of phthalic anhydride, and, according to GC analysis, 0.9 area % of N,N-dibutylcarbamoyl chloride. Based on the product, this corresponds to a crude yield of 97.8% of theory.

After fine distillation, 666.9 g of violet-coloured distillate having a product content of 95.2% by weight and a content of N,N-dibutylcarbamoyl chloride of still 0.9 area % is obtained as the main fraction at 85–113° C. and 0.05 to 0.2 mbar. This corresponds to a yield of 89.3% of theory.

Example 3 (Inventive: N,N-Dibenzylformamide as the Catalyst)

Catalyst Preparation:
300.0 g (1.48 mol) of dibenzylamine and 74.7 g (1.62 mol) of formic acid in 384.2 ml of toluene are initially charged at 20° C. This mixture is heated under reflux (95° C.) for one hour. For dewatering, the mixture is subsequently subjected to azeotropic distillation until no more water separates (total amount of water removed: 30.9 g). 671.2 g of toluene solution of the N,N-dibenzylformamide catalyst having a content of 49.5% are obtained. This corresponds to a yield of 99.9% of theory. The thus obtained catalyst solution (C1) is used below.

Reaction:
149.6 g (1.0 mol) of phthalic anhydride and 13.7 g (0.03 mol) of the above-described catalyst solution (C1) are initially charged in 620.9 ml of toluene, and the mixture is heated to 75° C. At this temperature, 296.8 g (3.0 mol) of phosgene at an introduction rate of 59.4 g of phosgene per hour and simultaneously 82.0 g of the C1 solution are added continuously (8.1 g of 100% N,N-dibenzylformamide per hour) over 5 hours. On completion of the metered addition of phosgene and catalyst, the mixture is stirred at 75° C. for a further 1.75 hours.

To remove excess phosgene, 253.6 g of distillate are removed at 55° C. and 60 mbar.

The crude product remains as a dark oil. It contains 69.7% by weight of phthaloyl chloride and 5.5% by weight of phthalic anhydride. This corresponds to a crude yield of 87% of theory.

After fine distillation at 100 to 104° C. and 0.3 mbar, 160.3 g of colourless distillate having a product content of 85.7% by weight are obtained as the main fraction. This corresponds to a yield of 67.6% of theory.

Example 4 (Inventive: N,N-dicyclohexylformamide as the Catalyst)

22.4 g (0.15 mol) of phthalic anhydride and 0.16 g (0.8 mmol) of N,N-dicyclohexylformamide as the catalyst are initially charged in 84.9 ml of toluene, and the mixture is heated to 75° C. At this temperature, 22.6 g (0.23 mol) of phosgene at an introduction rate of 9.0 g of phosgene per hour and simultaneously 1.73 g (0.01 mol) of N,N-dicyclohexylformamide dissolved in 19 ml of toluene are added uniformly (0.7 g of 100% N,N-dicyclohexylformamide per hour) over 150 minutes. On completion of the metered addition of phosgene and catalyst, the mixture is stirred at 75° C. for a further 2.5 hours.

To remove excess phosgene, 94 g of distillate are removed at 60° C. and 28 mbar.

The crude product remains as a dark oil. It contains 90.8% by weight of dichloride and 0.4% by weight of anhydride. This corresponds to a crude yield of 99.9% of theory.

After fine distillation at 98 to 100° C. and 0.1 to 1.2 mbar, 28.3 g of colourless distillate having a product content of 95.2% by weight are obtained as the main fraction. This corresponds to a yield of 88.5% of theory.

The invention claimed is:

1. A process for preparing phthaloyl chloride of the formula (I)

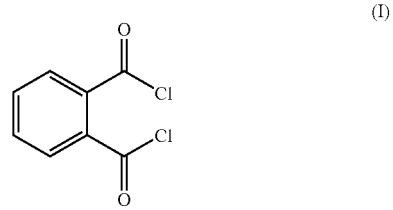

in which phthalic anhydride of the formula (II)

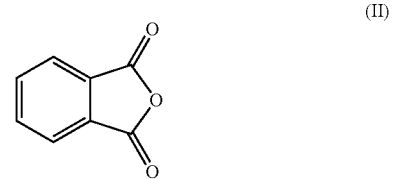

is reacted with phosgene in the presence of a catalyst, wherein the catalyst used is an N,N-disubstituted formamide of the general formula (III)

in which
$R^1$ and $R^2$ are each independently
  $C_3$–$C_8$-cycloalkyl,
  $C_6$–$C_{10}$-aryl or
  $C_7$–$C_{12}$-arylalkyl.

2. A process for preparing phthaloyl chloride of the formula (I)

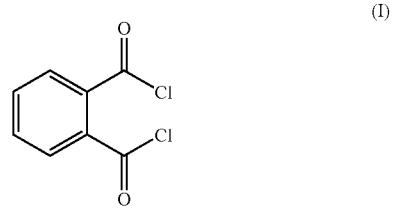

comprising:
reacting a phthalic anhydride of the formula (II)

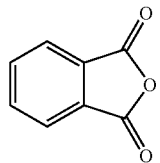
(II)

with phosgene in the presence of a catalyst;
wherein the catalyst used is an N,N-disubstituted formamide of the general formula (III)

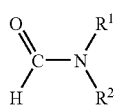
(III)

in which:
R$^1$ and R$^2$ are each, independently, a straight-chain or branched C$_8$–C$_{22}$-alkyl- or -alkenyl radical, wherein the total molecular weight of the N,N-disubstituted formamide is at least 269 g/mol.

3. The process according to claim 1, wherein the N,N-disubstituted formamide of the formula (III) used has an R$^1$ and R$^2$ which are each independently a C$_3$–C$_8$-cycloalkyl radical.

4. A process for preparing phthaloyl chloride of the formula (I)

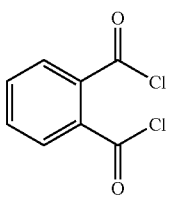
(I)

comprising:
reacting a phthalic anhydride of the formula (II)

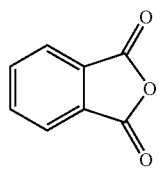
(II)

with phosgene in the presence of a catalyst:
wherein the catalyst used is an N,N-disubstituted formamide of the general formula (III)

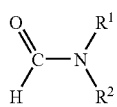
(III)

in which R$^1$ and R$^2$ are each independently a benzyl, phenyl, phenylpropyl, naphthyl, naphthylmethyl or naphthylethyl radicals.

5. The process according to claim 2, wherein the N,N-disubstituted formamide of the general formula (III) used is
N,N-dioctylformamide,
N,N-dinonylformamide,
N,N-didecylformamide,
N,N-diundecylformamide,
N,N-didodecylformamide,
N,N-ditridecylformamide,
N,N-ditetradecylformamide,
N,N-dipentadecylformamide,
N,N-dihexadecylformamide,
N,N-dioctadecylformamide,
N,N-dicyclopentylformamide,
N,N-dicyclohexylformamide,
N,N-dibenzylformamide,
N-methyl-N-benzylformamide or
N-methyl-N-naphthylmethylformamide.

6. The process according to claim 1, wherein the N,N-disubstituted formamides of the formula (III) are prepared by reacting the corresponding amine of the formula HNR$^1$R$^2$ where R$^1$ and R$^2$ may each be as defined for the formula (III) with formic acid.

7. The process according to claim 1, wherein 1.0 mol to 3.0 mol of phosgene are used for 1 mol of phthalic anhydride of the formula (II).

8. The process according to claim 1, wherein, based on 1 mol of phthalic anhydride of the formula (II), a total of 0.01–0.20 mol of N,N-disubstituted formamide of the formula (III) is used.

9. The process according to claim 1, wherein phthalic anhydride is initially charged in an inert diluent, and the phosgene and the N,N-disubstituted formamide of the formula (III) are subsequently each independently metered in continuously or "semi-continuously".

10. The process according to claim 9, wherein the N,N-disubstituted formamide of the formula (III) metered in is dissolved in an inert solvent which is selected from the inert solvent of the phthalic anhydride and a different inert solvent.

11. The process according to claim 1, wherein the phthalic anhydride is initially charged in an inert solvent together with the entire amount or a portion of the N,N-disubstituted formamide of the formula (III), the mixture is then heated to the reaction temperature and the phosgene and any remaining N,N-disubstituted formamide of the formula (III) are metered in continuously or "semi-continuously".

12. The process according to claim 1, wherein the N,N-disubstituted formamide of the formula (III) used has an R$^1$ and R$^2$ which are each the same C$_3$–C$_8$-cycloalkyl radical.

13. The process according to claim 1, wherein the N,N-disubstituted formamide of the formula (III) used has an R$^1$ and R$^2$ which are each a cyclopentyl or a cyclohexyl radical.

14. The process according to claim 2, wherein 1.0 mol to 3.0 mol of phosgene are used for 1 mol of phthalic anhydride of the formula (II).

15. The process according to claim 12, wherein 1.0 mol to 3.0 mol of phosgene are used for 1 mol of phthalic anhydride of the formula (II).

16. The process according to claim 2, wherein, based on 1 mol of phthalic anhydride of the formula (II), a total of 0.01–0.20 mol of N,N-disubstituted formamide of the formula(III) is used.

17. The process according to claim 12, wherein, based on 1 mol of phthalic anhydride of the formula (II), a total of 0.01–0.20 mol of N,N-disubstituted formamide of the formula (III) is used.

18. The process according to claim 9, wherein the N,N-disubstituted formamide of the formula (III) metered in is initially melted and then metered in as a melt.

* * * * *